(12) United States Patent
Rusly et al.

(10) Patent No.: US 8,323,272 B2
(45) Date of Patent: Dec. 4, 2012

(54) APPARATUS AND METHODS FOR PROGRAMMING A SHAPE-MEMORY MEDICAL DEVICE IMPLANT

(75) Inventors: Roy Junius Rusly, Lawrenceville, GA (US); Jhordan Gil, Norcross, GA (US)

(73) Assignee: Medshape Solutions, Inc.

( * ) Notice: Subject to any disclaimer, the term of this patent is extended or adjusted under 35 U.S.C. 154(b) by 472 days.

(21) Appl. No.: 12/706,747

(22) Filed: Feb. 17, 2010

(65) Prior Publication Data
US 2011/0202042 A1  Aug. 18, 2011

(51) Int. Cl.
*A61B 17/58* (2006.01)
*A61B 17/56* (2006.01)

(52) U.S. Cl. .............. 606/1; 148/95; 411/501

(58) Field of Classification Search .......... None
See application file for complete search history.

(56) References Cited

U.S. PATENT DOCUMENTS

| | | | |
|---|---|---|---|
| 5,120,175 A * | 6/1992 | Arbegast et al. | 411/501 |
| 5,419,788 A * | 5/1995 | Thoma et al. | 148/402 |
| 6,688,828 B1 | 2/2004 | Post | |
| 6,872,433 B2 | 3/2005 | Seward et al. | |
| 2008/0065074 A1 * | 3/2008 | Yeung et al. | 606/61 |
| 2008/0236601 A1 | 10/2008 | Jacobus | |
| 2009/0121391 A1 | 5/2009 | Gall et al. | |
| 2010/0028686 A1 * | 2/2010 | Xie | 428/413 |
| 2011/0257740 A1 * | 10/2011 | Shaoulian et al. | 623/2.37 |

FOREIGN PATENT DOCUMENTS
WO   WO 2006/116164 A1   11/2006

OTHER PUBLICATIONS

Siskind and Smith., 2008, "Model Development for Shape Memory Polymers," *Proc. SPIE 6929*: 69291II.

* cited by examiner

*Primary Examiner* — Henry M Johnson, III
*Assistant Examiner* — Scott T Luan
(74) *Attorney, Agent, or Firm* — Jones Day

(57) ABSTRACT

A medical device implant made with a shape-memory material is originally produced in a "permanent" configuration. The implant is then "programmed" into a temporary (typically smaller sized) configuration to facilitate implantation, after which, an external stimulus activates the implant to return to its permanent configuration. Apparatus and methods include inserting a first portion of the implant into an aperture of a compression fixture base, heating the implant, and then driving and compressing the remaining portion of the implant, which has a different, typically larger profile than that of the first portion, into the aperture with a compression fixture cover to "program" the remaining portion. The resulting programmed implant has first and remaining portions that have identical, or substantially identical, profiles.

9 Claims, 6 Drawing Sheets

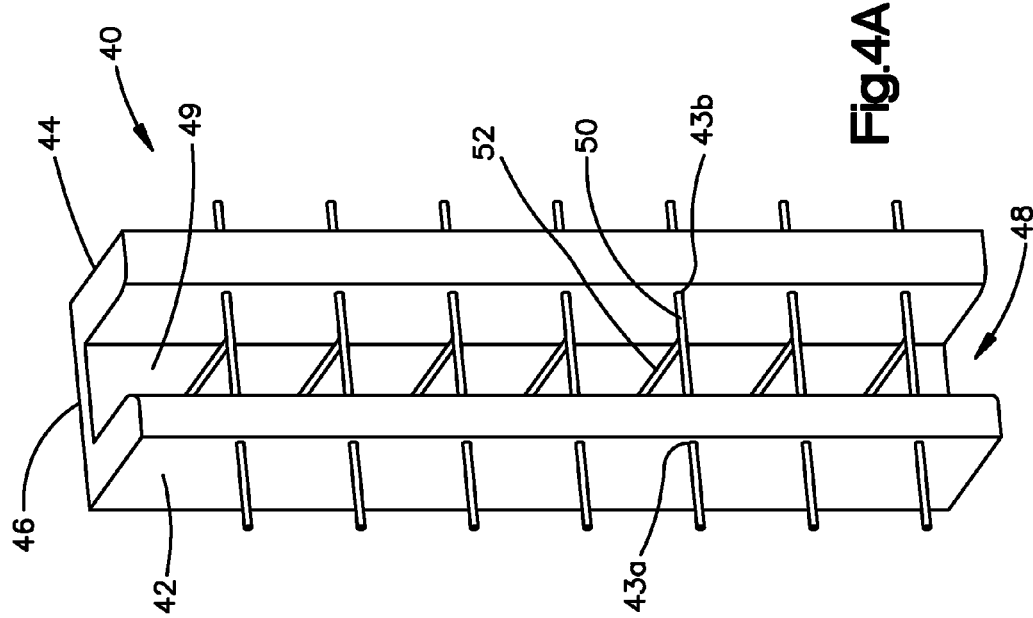
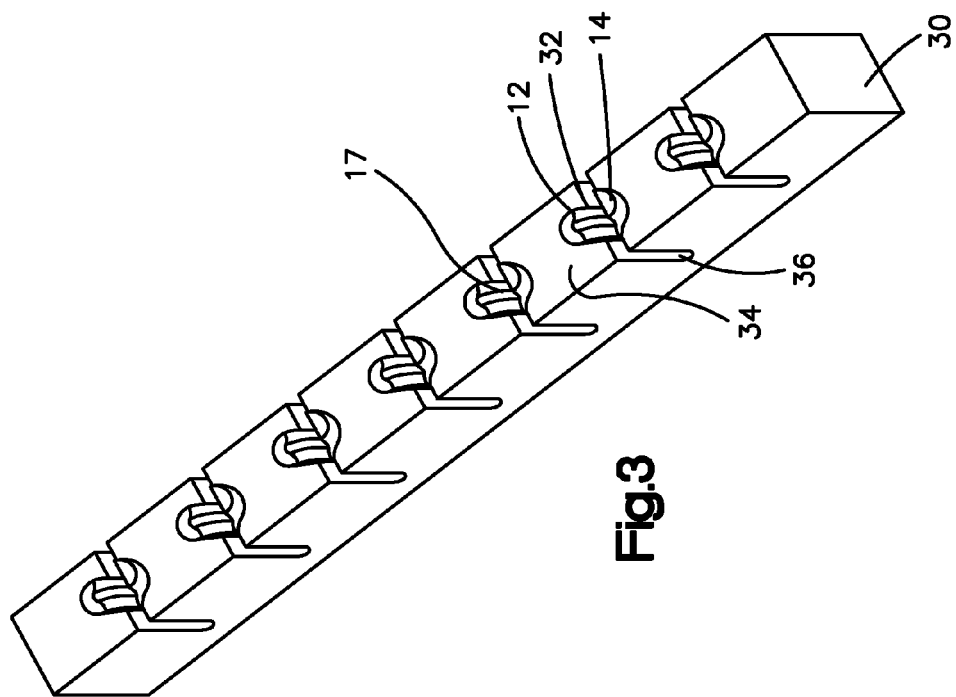

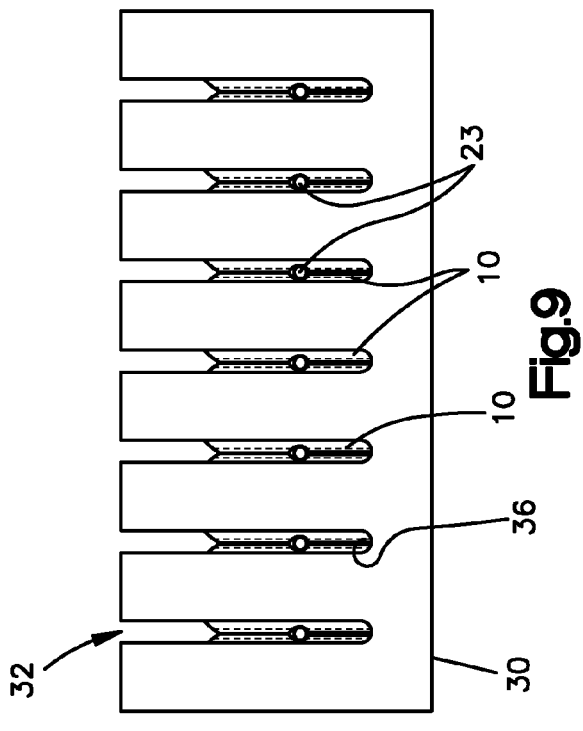
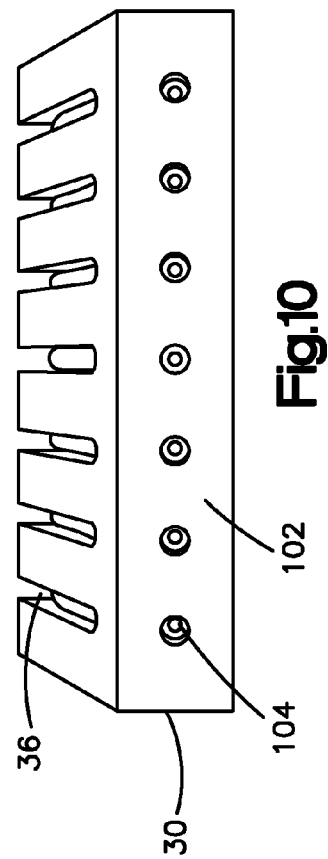
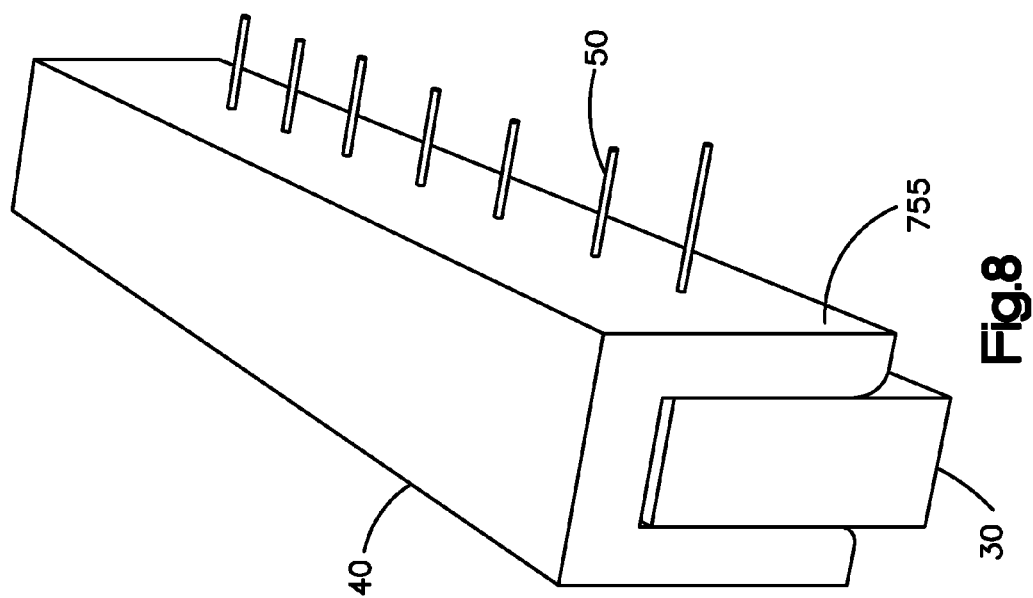

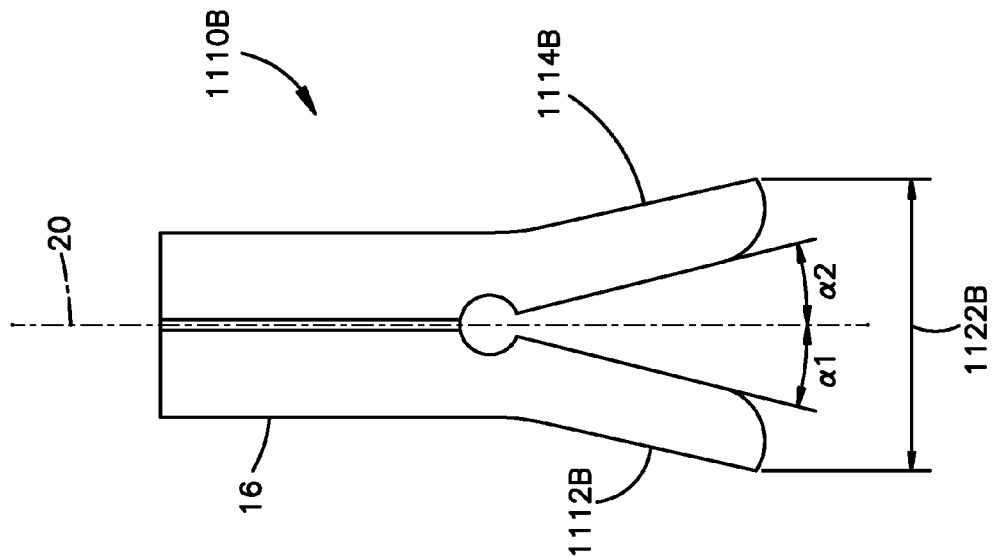
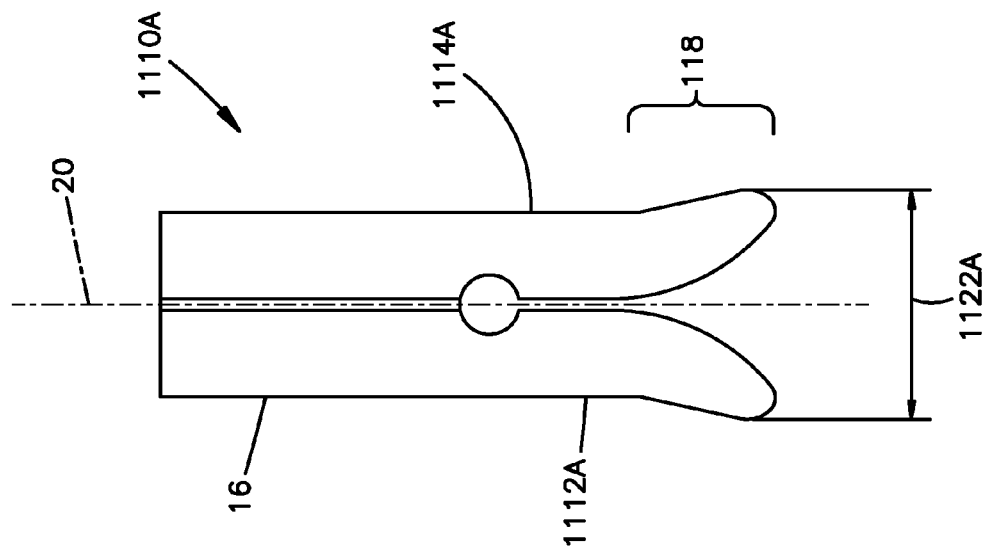

APPARATUS AND METHODS FOR PROGRAMMING A SHAPE-MEMORY MEDICAL DEVICE IMPLANT

FIELD OF THE INVENTION

The invention relates to medical device implants made from a shape memorizing polymer material that can be used as a base in osteo-implants and other in vivo surgical procedures requiring a stable locking base. More particularly, the invention relates to apparatus and methods of "programming" the medical device implant from a first permanent state into a second temporary state to facilitate deployment of the implant. After deployment, the medical device implant can be activated to change back into the first state.

BACKGROUND OF THE INVENTION

Shape-memory materials have the ability to change from a permanent or desired shape into a temporary transitional shape and then back into the permanent or desired shape. Shape-memory materials are stimuli-responsive in that they can change shape upon application of an external stimulus. These solid materials are initially formed into a "permanent" shape or configuration suited for their ultimate use. These materials can then be transformed into a transitional shape to facilitate, for example, implantation. Once implanted, an external stimulus (e.g., heat, light, chemical) can be applied to the material to transform the material back into its permanent shape or configuration. This process involves "programming" the shape-memory polymer from its permanent shape into a temporary shape and then "recovering" the permanent shape from the temporary shape.

In view of the advantages such materials provide, medical device implants are increasingly made with shape-memory materials. Typically, shape-memory materials are used so the implant can be temporarily reduced in size, thus requiring a smaller surgical entry site, and in the case of bone implants, smaller drilled holes in the bone. Smaller surgical entry sites and drilled holes lessen the invasiveness of the procedure and shorten recovery time.

When mass producing medical device implants made with shape-memory materials, a programming process should be conducted such that the devices are uniformly produced in their temporary shape without adversely affecting the devices' ability to transition back from the temporary shape to the permanent shape.

SUMMARY OF THE INVENTION

An object of the invention is to provide apparatus and methods of programming a medical device implant manufactured from a shape-memory polymer that results in consistently uniform products that retain their ability to effectively transition from the temporary shape to the permanent shape.

An example of a medical device implant manufactured from a shape-memory polymer that can be programmed by the invention has a first section or main body defining a central longitudinal axis there through. A second section comprising a pair of legs extends outward from the main body at respective angles to the central axis, forming a winged medical device implant. An interior channel is defined by the first and second legs and the main body. The interior channel opens to the ambient environment at the distal end of the first and second legs.

A compression fixture constructed in accordance with the invention is used to program the medical device implant. The compression fixture includes a base and a cover. The base has an aperture for receiving the medical device. The aperture has a cross section generally equal to the cross section of the main body of the medical device. The main body is positioned in the aperture such that the legs extend outward from the top of the aperture. The cover of the compression fixture is then positioned over the base. The cover has an engaging member that contacts the main body through the channel between the first and second legs. The compression fixture is then heated to a predetermined temperature for a predetermined period of time such that the polymeric material can be deformed without fracturing. The cover and base of the compression fixture are then compressed together (i.e., moved towards each other), causing the engaging member to drive the medical device further down into the aperture. This forces the first and second legs towards each other and into the aperture such that the legs are ideally, or at least substantially, parallel to the longitudinal axis. The compression fixture is then cooled, whereupon the cover and base are separated from each other. The "programmed" medical device can then be removed from the aperture in the base. The programmed medical device will retain the temporary "programmed" shape of the first and second legs compressed toward the longitudinal axis until acted upon by an external stimulus.

BRIEF DESCRIPTION OF THE DRAWINGS

The above and other advantages of the invention will be apparent upon consideration of the following detailed description, taken in conjunction with the accompanying drawings, in which like reference characters refer to like parts throughout, and in which:

FIG. 3 illustrates an embodiment of a base of a compression fixture loaded with medical device implants prior to being programmed according to the invention;

FIGS. 4A and 4B illustrate an embodiment of a cover of a compression fixture according to the invention;

FIG. 8 illustrates the compressed compression fixture after removal from the compression machine and thermal chamber;

FIG. 9 illustrates the base of the compression fixture containing the programmed medical devices implants within respective apertures of the base after removal of the cover;

FIG. 10 illustrates the bottom surface of the base of the compression fixture; and FIGS. 11A and 11B illustrate alternative embodiments of the medical device implant in its temporary state after being programmed.

DETAILED DESCRIPTION OF THE INVENTION

The invention relates to apparatus and methods of programming a medical device implant made with a shape-memory material. In particular, the medical device implant is manufactured from a shape-memory polymer and one example is a cross-linked methyl methacrylate (MMA) polymer that uses Memori™ 7111.

In one embodiment, the invention is used to program a medical device implant that is a "push-in" bone suture anchor. The suture anchor is used in various procedures for fixation of suture to bone in the shoulder, foot/ankle, knee, hand/wrist, and elbow. Such procedures include rotator cuff repair in the shoulder, medial collateral ligament repair in the knee, ulnar collateral ligament reconstruction in the hand/wrist, and tennis elbow repair. In each of these procedures, a hole is drilled into the bone and the medical device implant is positioned into the bone while in its programmed state. A stimulus (e.g., the heat from the body) activates the implant to return (e.g., expand) to its permanent shape, conforming the implant to its surroundings, which creates a stable locking base. This provides stronger fixation with less tissue damage than conventional means, such as, for example, surgical nails.

Figures 1A, 1B:
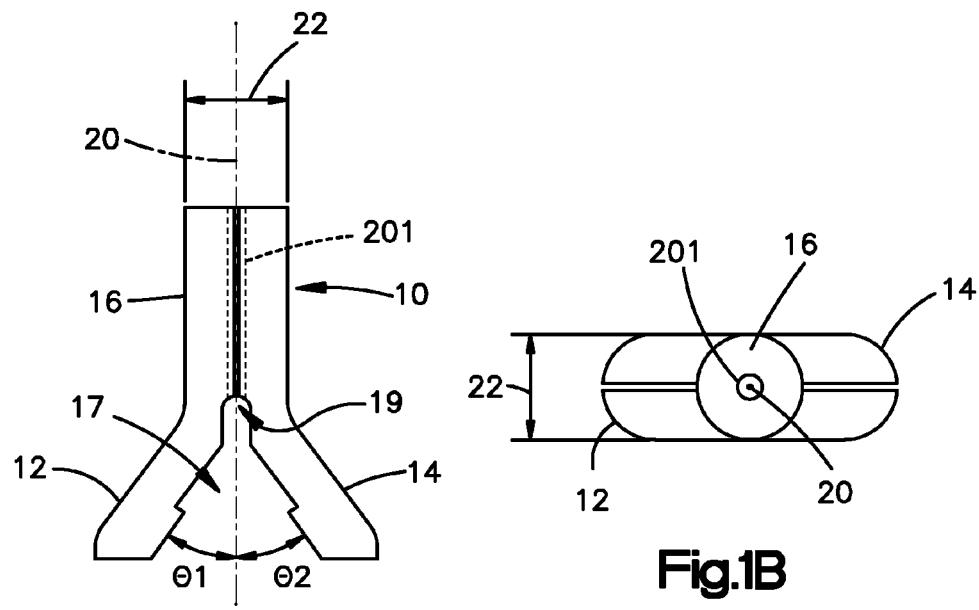
FIGS. 1A, 1B, and 1C illustrate elevational, top, and bottom views, respectively, of an embodiment of a medical device implant in its permanent state prior to being programmed.
Figure 1C:
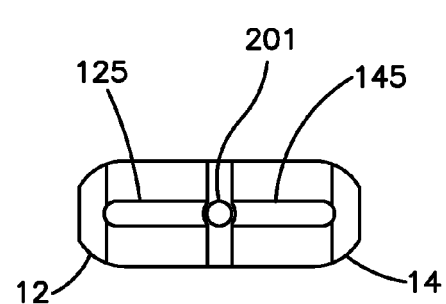

FIGS. 1A-1C show winged medical device implant 10, which is a bone suture anchor that can be used in orthopedic procedures. Medical device 10 has a left leg 12 and right leg 14 which both extend from a main body 16. Main body 16 has a central longitudinal axis 20 and a width 22. Extending through main body 16 is an optional through-bore 201. Left leg 12 and right leg 14 extend downward and outward from main body 16 at respective angles Ø1 and ØØ2 formed with axis 20. The angles are preferably equal and preferably each about 35°, but may range from about 30° to 40°. Each leg extends outward beyond the peripheral profile of main body 16 as viewed from the top of main body 16 in the direction of axis 20. A channel 17 and interior space 19 are defined between left leg 12, right leg 14, and main body 16. As shown in FIG. 1C, each leg 12, 14 has an optional semi-circular groove 125, 145 on its inner face in channel 17 that extends from the end of the leg to interior space 19. This configuration of medical device implant 10 illustrates its permanent shape which, as shown, forms an inverted Y-shaped structure. Alternatively, other shapes are possible depending on the application.

Figure 2:
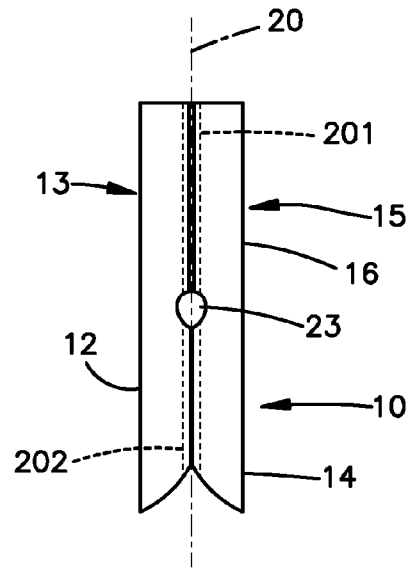
FIG. 2 illustrates an elevational view of an embodiment of the medical device implant in its temporary state after being programmed.

FIG. 2 illustrates medical device 10 in its programmed state. In this state, left leg 12 and right leg 14 have been programmed to be generally aligned with main body 16 such that the outer periphery of main body 16 and left leg 12 form a substantially, if not completely, common linear profile 13 on a left side of medical device 10, while the outer periphery of main body 16 and right leg 14 form a substantially, if not completely, common linear profile 15 on a right side of medical device 10. By providing such common profiles, deployment of medical device 10 in vivo can be made with a smaller incision and a smaller drilled hole in bone than if made with the legs of device 10 extended in their permanent position. In the programmed configuration, legs 12 and 14 are compressed together such that grooves 125 and 145 meet to create a through-bore 202 having a diameter preferably equal to the diameter of through-bore 201 in main body 16. This creates a through-bore extending the entire length of programmed medical device 10, which is used to load the programmed device onto or into certain implant/deployment tools. Note that all embodiments of medical device 10 do not require such a through-bore.

In the programmed state, a lateral through-hole 23 passing through medical device 10 is formed at interior space 19. Through-hole 23 is preferably defined within medical device 10 by legs 12 and 14 and main body 16 and, in a preferred embodiment, is laterally aligned where legs 12 and 14 extend from main body 16 (i.e., at the crotch of legs 12 and 14). Alternatively, through-hole 23 may be positioned solely within, and may be defined solely by, main body 16. Lateral through-hole 23 is used during the programming process (see further below).

FIG. 3 shows an embodiment of a base of a compression fixture for programming medical device implant 10 in accordance with the invention. Base 30 has a plurality of apertures 32 extending inward from top surface 34. Each aperture is sized to mirror the cross section of main body 16 of medical device 10. The depth of each aperture should be longer than medical device 10 as measured along longitudinal axis 20. Depending on the pre-programmed shape of medical device 10, apertures 32 may be cylindrical bores. Alternatively, apertures 32 may be of other shapes or configurations in accordance with the particular pre-programmed shape of medical device 10. Apertures 32 also include slots 36 that extend down from top surface 34 and extend from one side of base 30 through to the opposite side. The depth of slots 36, as measured down from top surface 34, can be equal to or greater than the depth of aperture 32, but in no case should the slots be less than that depth by more than the length of main body 16 as measured along the longitudinal axis.

FIG. 3 also shows the main body 16 of each medical device implant 10 inserted at least partially into a respective aperture 32. In a preferred embodiment, apertures 32 are configured such that main body 16 engages the aperture walls (i.e., the inner surface of base 30 forming the perimeter of aperture 32). While tolerances may vary in the manufacturing of base 30 and apertures 32, a tight fit is preferred between main body 16 and base 30 when main body 16 is received within aperture 32. With main body 16 received within aperture 32 as shown, legs 12 and 14 of medical device 10 (in its permanent state) abut top surface 34 of base 30 at opposite perimeter edges of aperture 32 and extend outward and above top surface 34. In this position, channel 17 is open to the ambient environment at the top of base 30.

Figure 4B:
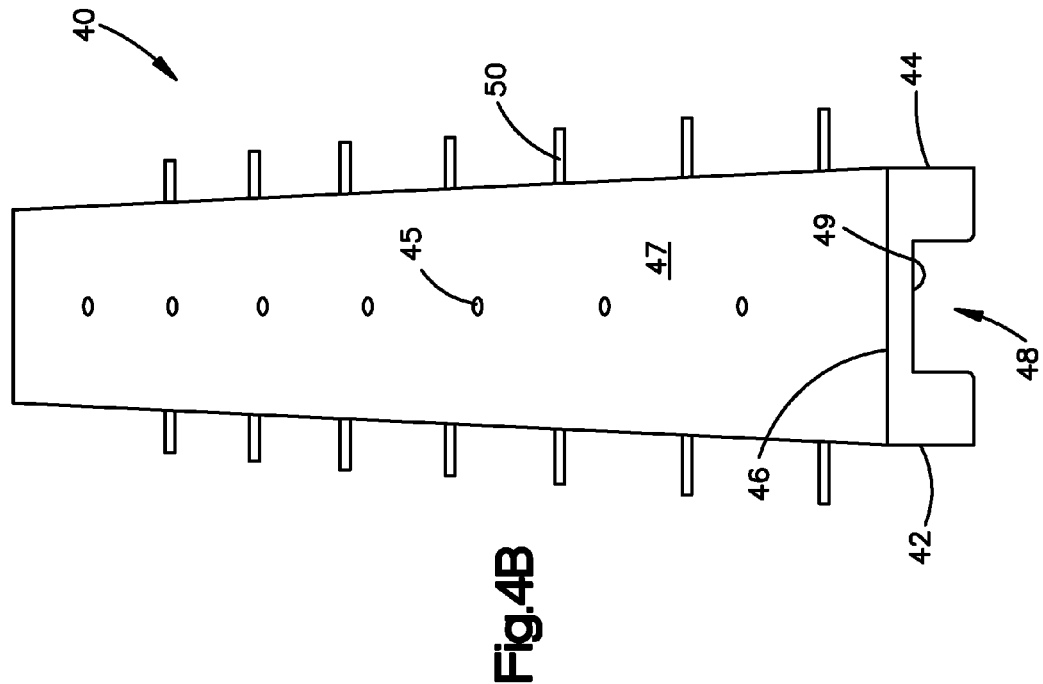

FIGS. 4A and 4B show an embodiment of a compression fixture cover for programming medical device 10 in accordance with the invention. Cover 40 is a generally U-shaped structure having a left side 42, a right side 44, and a connecting top side 46. The left and right sides are spaced apart from each other to form a channel 48 for receiving base 30. Traversing the space between the left and ride sides of cover 40, and carried by the left and right sides, are a plurality of engaging members 50. In this embodiment, engaging members 50 are rods or pins that extend across and through the distal ends of left side 42 and right side 44. Depending on the configuration of the medical device implant to be programmed, engaging members 50 alternatively may be other types of structures and their position across channel 48 may vary. Each engaging member 50 is received within a hole 43a in left side 42 and a corresponding hole 43b in right side 44. Corresponding pairs of holes 43a,b are preferably aligned, and engaging members 50 preferably extend parallel to top side 46. Each engaging member 50 is individually removable through holes 43a,b.

Cover 40 also preferably includes a plurality of gage members 52 that extend into channel 48 from top side 46. In this embodiment, gage members 52 are inserted into respective through-holes 45 in top side 46 and are pins or rods, but alternatively may be other types of structures depending on the configuration of the medical device to be programmed. Gage members 52 are received in through-holes 45 such that they do not protrude above top surface 47 of cover 40. Each gage member 52 is long enough to contact and abut (i.e., sit on) a respective engaging member 50 without protruding above top surface 47. Gage members 52 are not permanently attached to engaging members 50, but may be permanently attached to cover 40 by any known means and, accordingly, may not require through-holes 45. In this embodiment, each gage member 52 is oriented preferably perpendicularly to a respective engaging member 50, forming an inverted T-shaped structure within channel 48.

Figure 5:
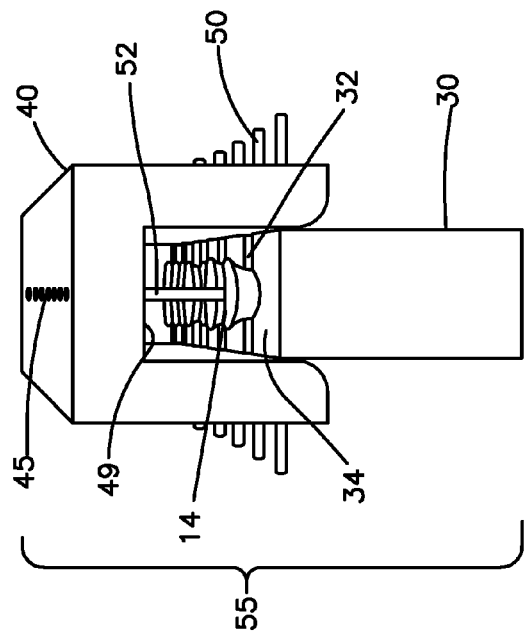
FIG. 5 illustrates a loaded compression fixture prior to programming of the medical device implant according to the invention.

FIG. 5 shows cover 40 positioned over base 30 with channel 48 partially receiving base 30. Engaging members 50 are received within respective channels 17 of medical device implants 10 (which were previously loaded into apertures 32 of base 30). In this position, engaging members 50 are preferably received within channels 17 deep enough to contact main body 16 at interior space 19 (i.e., the crotch of left and right legs 12 and 14). This allows cover 40 to maintain the position shown with respect to base 30, wherein no part of cover 40 contacts any portion of left and right legs 12 and 14 extending above aperture 32. The assembly of cover 40 and base 30 as shown may be referred to as a loaded compression fixture 55.

Figure 6:
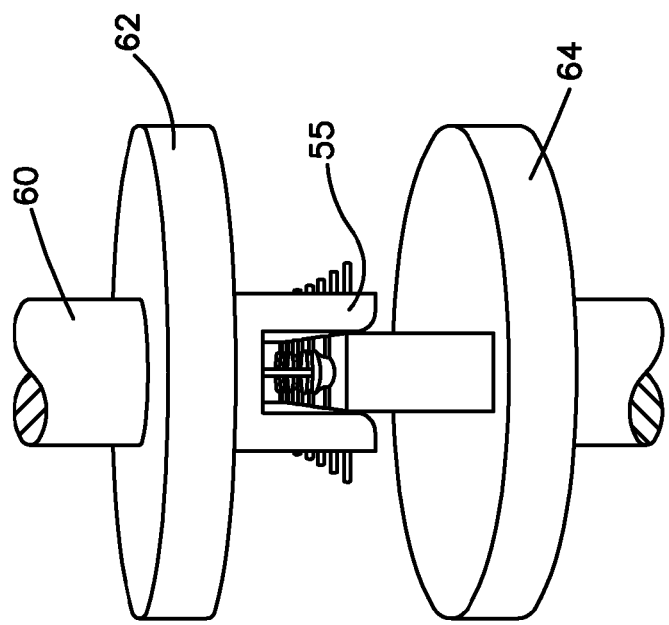
FIG. 6 illustrates the loaded compression fixture placed between compression plates of a compression machine within a thermal chamber according to the invention.

To program the medical device, loaded compression fixture 55 is placed in a compression machine, which is positioned in a thermal chamber. FIG. 6 shows compression fixture 55 placed in a compression machine 60 between compression plates 62 and 64. A suitable compression machine is a Model No. 5567-Q5039 by Instron® of Norwood, Mass. Compression machine 60 is positioned in a thermal chamber 70, which is better seen in FIG. 7. A suitable thermal chamber is an Instron® SFL Model No. 3282. Thermal chamber 70 should be capable of producing a maximum internal temperature of about 190 degrees Celsius. However, depending on the type of shape-memory material used, this maximum temperature may be much lower.

Compression fixture 55 should be allowed to equilibrate in thermal chamber 70 to a set temperature. The set temperature can vary widely depending on the shape-memory material used. For example, the set temperature for a cross-linked methyl methacrylate (MMA) polymer can range from about 30 degrees Celsius to about 190 degrees Celsius, depending on the specific composition. Equilibration time can range from about one minute to about 30 minutes, again depending on the shape-memory material and the set temperature.

Once the temperature of compression fixture 55 has equilibrated, compression plate 62 is brought towards compression plate 64 (alternatively, depending on the compression machine, both plates may be brought together simultaneously, or plate 64 may be brought towards plate 62). As plates 62 and 64 are brought together, cover 40 moves down over base 30, which in turn causes engaging members 50 to drive medical devices 10 further into apertures 32. As device 10 is driven further into aperture 32, left leg 12 and right leg 14 are compressed towards each other (i.e., inwards) as they are forced into aperture 32. This movement aligns left leg 12 and right leg 14 with main body 16. Gage members 52, which move with cover 40 and engaging members 50, maintain a uniform diameter through-bore 202 between and along the entire length of compressed legs 12 and 14 as grooves 125 and 145 are compressed towards each other and around gage member 52. Through-bore 202 replaces channel 17. Preferably, engaging member 50 contacts main body 16 across the entire width of main body 16 as cover 40 is driven downward by compression plate 62. By contacting the entire width of main body 16, the downward force applied by engaging member 50 is preferably evenly distributed across medical device 10 such that left leg 12 and right leg 14 descend into aperture 32 at an equal rate. This equal rate of descent along with gage member 52 results in a symmetrical programmed device. As the entire medical device 10 is received within aperture 32, left leg 12 and right leg 14 are each compressed and subjected to a strain of at least 15 percent and preferably 22 to 30 percent as measured from the permanent state. "Strain" may be defined as a forced change in the dimensions of a body.

Figure 7:
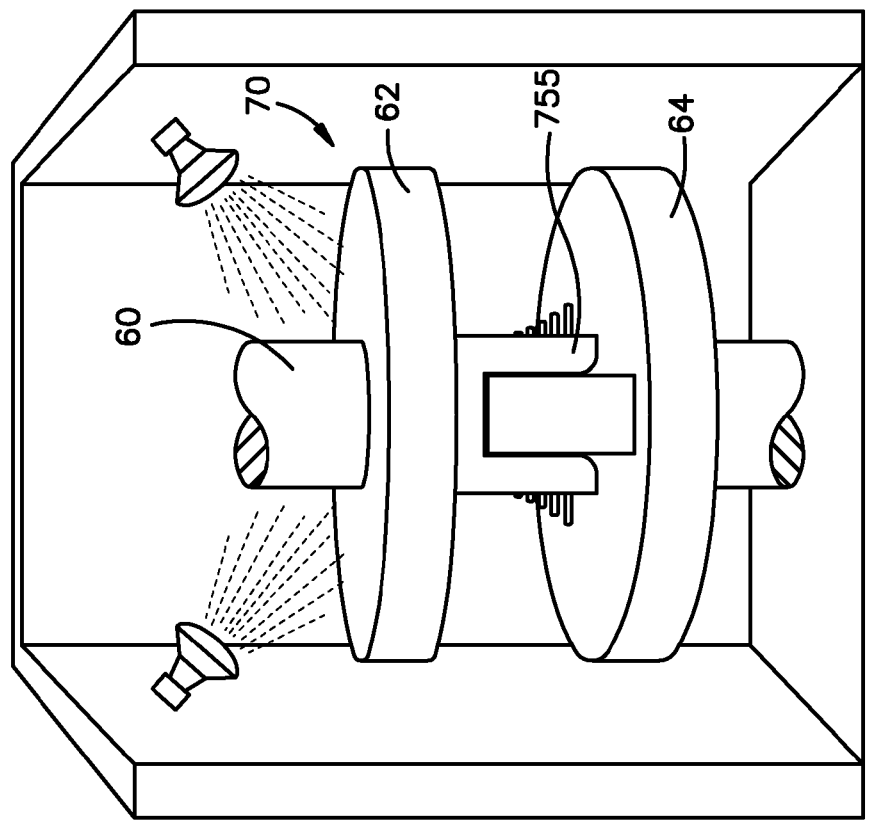
FIG. 7 illustrates the compression fixture after the cover and base have been compressed together according to the invention.

FIG. 7 shows the compression fixture fully compressed within the compression machine and thermal chamber. That is, inside surface 49 of top side 46 of cover 40 butts against top surface 34 of base 30. Accordingly, the distance between inside surface 49 and the engaging members 50 should be such that the entire medical device implant 10 is fully received within aperture 32 when inside surface 49 butts against top surface 34 of base 30. Note that for other medical device implants and/or embodiments of the invention, cover 40 need not butt against base 30. Cover 40 need only move toward base 30 enough to ensure that either the entire medical device implant or a sufficient amount or length of the medical device implant has been driven into aperture 32 such that the desired programming can be accomplished.

Once medical device implants 10 have been heated and compressed, compression fixture 755 is removed from compression machine 60 and thermal chamber 70 and allowed to cool to preferably 20° to 30° Celsius and more preferably to about 27° Celsius. Compression fixture 755 may be placed in a freezer to accelerate cooling. The time in the freezer may be about 20 minutes, depending on the temperature in the freezer. FIG. 8 shows compression fixture 755 removed from the compression machine and thermal chamber.

After the compression fixture and medical devices have cooled sufficiently, engaging members 50 are preferably first removed from cover 40. In this embodiment, engaging members 50 are rods or pins that are pushed through holes 43$a,b$ in right and left sides 42 and 44 and through-hole 23, which formed at interior portion 19 of medical device implant 10 when legs 12 and 14 were compressed together. Through-hole 23 provides a space for engaging member 50 so the legs can be compressed together without damaging the implant. Removal of engaging members 50 allows cover 40 to be removed from base 30 without disturbing the medical device implants within apertures 32.

Alternatively, cover 40 may be removed from base 30 without first removing engaging members 50. However, much more force is required to separate cover 40 from base 30, and there is a risk of bending engaging members 50 and/or damaging or disrupting the symmetry of programmed legs 12 and 14. Thus, removing cover 40 without first removing engaging members 50 is not recommended.

Upon removal of cover 40 from base 30, most, if not all, vertical gage members 52 will be held between the compressed legs 12 and 14 of the medical device implant. Gage members 52 may then be pulled out from between the legs through the newly created through-bore 202. Note that some gage members 52 may remain frictionally attached to cover 40 upon cover 40's removal from base 30, depending on the respective diameters of the gage member and through-hole 45 in top side 46. These tight-fitting gage members are thus pulled out from the programmed medical device implants as cover 40 is separated from base 30. The same is true for those gage members 52 that are permanently attached to cover 40.

FIG. 9 shows base 30 with programmed medical device implants 10 completely contained within respective apertures 32. Because apertures 32 have a depth greater than the length of medical device 10, each medical device 10 is driven completely into a respective aperture upon the cover's inner surface 49 engaging the base's top surface 34. The medical devices 10 are driven into the apertures by engaging members 50, which also travel downward as cover 40 travels downward over base 30 during the compression process.

FIG. 10 shows the bottom surface 102 of base 30. Bottom surface 102 has removal apertures 104 respectively aligned with and extending through to apertures 32. Medical device implants 10 can be removed from base 30 with a removal device, such as, for example, a pin gage or an appropriately sized rod, inserted into a removal aperture 104 to urge a programmed medical device implant 10 from a respective aperture 32. The medical device implant is removed in its programmed state, as shown in FIG. 2. Preferably, the deflection of the legs in the programmed state represents a strain of at least 15 percent and preferably 22 to 30 percent as measured from the permanent state.

Base 30 and cover 40 are each preferably made of aluminum 6061 but, alternatively, may be made of any equally strong or stronger alloy/metal or other material capable of withstanding (i.e., maintaining their shape and structural integrity when subjected to) the heating, compression, and cooling described above.

Engaging members 50 and gage members 52 are each preferably made of heat treated tool steel but, alternatively, may be made of any equally strong or stronger metal or other material capable of withstanding (i.e., maintaining their shape and structural integrity when subjected to) the heating, compression, and cooling described above.

While a preferred embodiment of the invention has been described and disclosed, modifications to the apparatus and methods described herein are possible within the scope of the invention. For example, although base 30 has been shown as a generally elongated rectangular block, the shape of base 30 is not limited to that shape. For example, base 30 may have a cylindrical, cubical, ellipsoidal, or trapezoidal shape. The configuration of base 30 may depend at least in part on the type and/or size of medical device implant to be programmed, and the manner in which the implant is to be programmed.

Similarly, cover 40 has been shown as a generally elongated U-shaped structure. Cover 40, however, is not limited to such a shape. So long as cover 40 mates with base 30 in a manner that allows cover 40 and base 30 to be compressed together by a compression machine to accomplish the desired programming of a medical device implant, cover 40 may be of other shapes or configurations.

Note also that although the compression fixture has been shown and described such that a plurality of identical medical device implants 10 can be simultaneously programmed by base 30 and cover 40, the invention is not limited in this way. For example, a compression fixture in accordance with the invention may only accommodate a single medical device implant for programming, or may alternatively accommodate a plurality of different medical device implants for simultaneous programming wherein individual apertures of base 30 and corresponding engaging members of cover 40 may be customized in accordance with the particular medical device implant to be programmed.

Furthermore, while legs 12 and 14 are programmed to define a common plane or profile (e.g., profiles 13 and 15) with main body 16 along preferably the entire length of medical device 10 from one end of the main body to the distal ends of the respective legs as shown in FIG. 2, legs 12 and 14 may be compressed from their permanent position to their programmed position to a degree which does not render the legs fully coplanar with the main body or perfectly parallel with longitudinal axis 20 either for the entire length of the legs or for only a portion of the length of the legs. For example, FIG. 11A shows an embodiment of a programmed medical device implant 1110A, wherein left leg 1112A and right leg 1114A each forms a common plane or profile with main body 16 for only a portion of the respective lengths of the legs. A short distal portion 118 of each leg is bent slightly outwards from the main body. That is, most, but not all, of the length of the left and right legs are parallel to axis 20.

Similarly, FIG. 11B shows another embodiment of programmed medical device implant 1110B, wherein left leg 1112B and right leg 1114B are only substantially coplanar with main body 16 or substantially parallel to axis 20. That is, angles α1 and α2 are small and substantially less than angles Ø1 and Ø2 (see FIG. 2) and may range, for example, from 0+° to 5°.

Another way to describe the slightly less than ideal programmed state of the medical device implant embodiments shown in FIGS. 11A and 11B is to define the widths 1122A and 1122B of the implants at the respective distal ends of the legs as being no more than 10% greater than width 22 (see FIGS. 1A and 1B). In any case, the programmed legs of the medical device implant are subject to a strain which is released when the programmed medical device implant is activated to return to its permanent state. Preferably, the left and right legs are subjected to a strain of at least 15 percent and preferably 22 to 30 percent as measured from their permanent state.

Thus it is seen that apparatus and methods for programming a shape-memory medical device implant are provided. One skilled in the art will appreciate that the invention can be practiced by other than the described embodiments, which are presented for purposes of illustration and not of limitation, and the invention is limited only by the following claims.

We claim:

1. A method of programming a medical device implant made with a shape-memory polymer, the implant being in a first state and having a main body, a central longitudinal axis through the body, a first leg extending outward from the body at an angle with respect to the longitudinal axis, and a second leg extending outward from the body at an angle with respect to the longitudinal axis, the method comprising:

inserting the main body of the medical device implant into an aperture of a base, the aperture having a cross section generally equal to the cross section of the main body;

engaging the main body with an engaging member;

heating the medical device implant for a predetermined time while the main body is inserted in the aperture and the engaging member engages the main body;

moving the engaging member such that the first and second legs are fully received within the aperture; and compressing the first and second legs around a gage member to form a through-bore between the first and second legs upon removal of the gage member;

cooling the medical device implant; and removing the medical device implant from the base, the medical device implant being in a second state wherein the first and second legs are at least substantially parallel to the longitudinal axis.

2. A method of programming a medical device implant made with a shape-memory material, the implant having a first section and a second section, the second section having a profile different than the profile of the first section, the method comprising:

inserting the first section in an aperture, the aperture having a profile substantially identical to the first section;

heating the first and second sections to a predetermined temperature for a predetermined period of time;

driving the first section further into the aperture to force the second section into the aperture;

subjecting the second section to a strain of at least 15 percent as measured prior to the second section being forced into the aperture; and removing the medical device implant from the aperture, wherein the first and second sections have profiles that are substantially identical.

3. Apparatus for programming a medical device implant made with a shape-memory material, the implant having a first section and a second section, the second section having a profile different than the profile of the first section, the apparatus comprising;
 a base having an aperture in a first surface of the base, the aperture sized to receive the first section; and
 a cover having a first side, a second side, and a connecting side forming a channel between the first and second sides, the channel sized to receive the base there between, the cover forming a U-shaped structure and also having an engaging member extending across the channel; wherein:
 a first surface of the connecting side is configured to be compressed against the first surface of the base; and
 the base and cover are operative to withstand temperatures up to about 190 degrees Celsius.

4. The apparatus of claim 3 wherein:
 the base has a second surface opposite the first surface of the base;
 the connecting side has a second surface opposite the first surface of the connecting side; and
 the second surface of the base and the second surface of the cover are configured to mate with respective compression plates of a compression machine.

5. The apparatus of claim 3 wherein the aperture comprises a cylindrical bore sized to receive the first section of the medical device implant.

6. The apparatus of claim 3 wherein the aperture comprises a slot extending across the first surface of the base from a third surface of the base to an opposite fourth surface of the base, the slot sized to receive the engaging member.

7. The apparatus of claim 3 wherein the engaging member is a pin or rod inserted through respective holes in the first and second sides of the cover, the pin or rod oriented parallel to the connecting side.

8. The apparatus of claim 3 further comprising a gage member extending into the channel from the connecting side, one end of the gage member in contact with the engaging member, the gage member operative to form a through-bore in the second section of the medical device implant.

9. The apparatus of claim 3 wherein the base has a second surface opposite the first surface of the base, the second surface having a removal hole in communication with the aperture, the removal hole sized to receive a removal tool for pushing a programmed medical device implant out through the aperture on the first surface.

* * * * *

UNITED STATES PATENT AND TRADEMARK OFFICE
CERTIFICATE OF CORRECTION

PATENT NO.        : 8,323,272 B2                                      Page 1 of 1
APPLICATION NO.   : 12/706747
DATED             : December 4, 2012
INVENTOR(S)       : Rusly et al.

It is certified that error appears in the above-identified patent and that said Letters Patent is hereby corrected as shown below:

Title page, item [73] change assignee from "Medshape Solutions, Inc." to
--MedShape, Inc.--.

Signed and Sealed this
Twenty-second Day of January, 2013

David J. Kappos
*Director of the United States Patent and Trademark Office*